United States Patent
Wu et al.

(10) Patent No.: US 7,697,976 B2
(45) Date of Patent: Apr. 13, 2010

(54) NON-EVASIVE METHOD AND APPARATUS OF DETECTION OF ORGANISM TISSUES

(75) Inventors: Jinguang Wu, Beijing (CN); Yuanfu Zhang, Changchun (CN); Yizhuang Xu, Beijing (CN); Qingbo Li, Beijing (CN); Shifu Weng, Beijing (CN); Limin Yang, Beijing (CN); Li Zhang, Beijing (CN); Weijin Zhou, Beijing (CN); Zhanlan Yang, Beijing (CN); Weihong Li, Beijing (CN); Huizhong Wu, Beijing (CN); Rongye Gong, Beijing (CN); Xuejun Gao, Beijing (CN); Duanfu Xu, Beijing (CN); Ying Zhao, Beijing (CN); Zhi Xu, Beijing (CN); Nengwei Zhang, Beijing (CN); Lixin Wang, Beijing (CN); Kaihua Sun, Beijing (CN); Xin Peng, Beijing (CN); Yufeng Liu, Beijing (CN); Xuejun Sun, Xi'an (CN); Xiaofeng Ling, Beijing (CN); Su Zhou, Beijing (CN); Zhi Liu, Beijing (CN); Guoqiao Lai, Wenyi Road (CN); Jianxiong Jiang, Wenyi Road (CN); Qinghua Pan, Wenyi Road (CN); Qiguang Wu, Haidian District (CN); Guangyan Yu, Haidian District (CN); Bingbing Wang, Beijing (CN)

(73) Assignees: Peking University, Beijing, P.R. (CN); Beijing Second Optical InstrumentFacotry, Beijing, P.R. (CN)

( * ) Notice: Subject to any disclaimer, the term of this patent is extended or adjusted under 35 U.S.C. 154(b) by 761 days.

(21) Appl. No.: 10/586,272
(22) PCT Filed: Jan. 18, 2005
(86) PCT No.: PCT/CN2005/000079

§ 371 (c)(1),
(2), (4) Date: Jul. 18, 2006

(87) PCT Pub. No.: WO2005/072599

PCT Pub. Date: Aug. 11, 2005

(65) Prior Publication Data

US 2008/0228083 A1    Sep. 18, 2008

(30) Foreign Application Priority Data

Jan. 19, 2004 (CN) .................. 2004 1 00011093

(51) Int. Cl.
A61B 5/02 (2006.01)
(52) U.S. Cl. .................................................. 600/473
(58) Field of Classification Search ................ 600/473, 600/476, 478
See application file for complete search history.

(56) References Cited

U.S. PATENT DOCUMENTS 4,922,104 A * 5/1990 Eguchi et al. .......... 250/339.08
(Continued)

FOREIGN PATENT DOCUMENTS

CN      1194133 A    9/1998
(Continued)

OTHER PUBLICATIONS

Spectroscopy and Spectral Analysis; May 2004, vol. 24, No. 5, pp. 628-630 (non-translated). (Continued)

*Primary Examiner*—Eric F Winakur
*Assistant Examiner*—Joel F Brutus
(74) *Attorney, Agent, or Firm*—Westman, Champlin & Kelly, P.A.

(57) ABSTRACT

The invention relates to a non-invasive method to diagnose the changes of molecular structures of organism tissues from body surface and a dedicated apparatus. The apparatus is comprised of a Fourier Transform infrared spectrometer and a set of additional accessories. Said additional accessories include a mid-IR fiber optics sampling attachment, a fiber coupling part, and an infrared detector part. The detection method is comprised of placing the ATR probe of the dedicated apparatus on the skin surface of a region to be tested, and scanning more than one time in which the resolution of the apparatus is 1-32 $cm^{-1}$ and the range of the spectrum is 800-4000 $cm^{-1}$. It is possible to detect changes in molecular structures of living biological tissues in the early stages of cancer, and testees will not feel uncomfortable during testing. The method is easy to operate, quick, accurate, and it doesn't harm the body.

21 Claims, 6 Drawing Sheets

U.S. PATENT DOCUMENTS

| | | | |
|---|---|---|---|
| 5,803,082 A * | 9/1998 | Stapleton et al. | 600/407 |
| 5,818,996 A * | 10/1998 | Doyle | 385/115 |
| 6,574,490 B2 | 6/2003 | Abbink et al. | 600/316 |
| 2001/0048077 A1* | 12/2001 | Afanassieva | 250/339.08 |
| 2002/0072676 A1 | 6/2002 | Afanassieva | 600/473 |
| 2002/0164810 A1* | 11/2002 | Dukor et al. | 436/64 |

FOREIGN PATENT DOCUMENTS

| | | |
|---|---|---|
| CN | 1397794 A | 2/2003 |
| CN | 1444726 A | 9/2003 |

OTHER PUBLICATIONS

"Distinguishing Malignant from Normal Oral Tissues Using FTIR Fiber-Optic Techniques"; Wu et al.; Biopolymers (Biospectroscopy), vol. 62, pp. 185-192; 2001.

Spectroscopy and Spectral Analysis; Oct. 1996; vol. 16, No. 5, pp. 22-25.

Infrared Characterization of Nuclei Isolated from Normal and Leukemic (B-CLL) Lymphocytes: Part III; Benedetti et al.; vol. 40, No. 1,1986; pp. 39-43.

* cited by examiner

NON-EVASIVE METHOD AND APPARATUS OF DETECTION OF ORGANISM TISSUES

CROSS-REFERENCE TO RELATED APPLICATION

This Application is a Section 371 National Stage Application of International Application No. PCT/CN2005/000079, filed Jan. 18, 2005 and published as WO 2005/072599 on Aug. 11, 2005, not in English, the content of which is hereby incorporated by reference.

BACKGROUND OF THE INVENTION

1. Field of Invention

The present invention relates to a method of body surface non-invasive detection of changes in molecular structures of organism tissues, and also relates to a dedicated apparatus for detecting changes in molecular structures of organism tissues.

2. Description of Prior Art

Survival for cancer patients depends largely on early detection. Thus, an important goal in cancer research is to develop accurate, quick, convenient and inexpensive methods to detect cancer early. Iconography methods, e.g. CT and MRI etc, to detect pathologic changes inside the human body via the "space-occupying effect" are now commonly used in clinics. A restriction of these methods is that a lesion cannot be detected before it has attained a large enough size (>1 cm in diameter). Concerning endoscopic and biopsy methods, a disadvantage is that patients may suffer from the long, invasive sampling process. Therefore, alternative approaches for early diagnosis of cancer are needed.

Infrared spectroscopy is a sensitive probe to reflect molecular structure. It is known that every substance has its own characteristic infrared spectrum, i.e. only absorbing infrared rays of some wavelengths but not other wavelengths, so the characteristic infrared absorption spectrum can be used for qualitative analysis of the substance. Moreover, the concentration of one component is proportion to the absorbance, so the characteristic infrared absorption spectrum can also be used for quantitative analysis of the substance. At present, infrared spectrometers are often used to measure absorbance (or transmittance) of substances to infrared radiations to study changes of molecular structure. Organism tissues comprise nucleic acid, poly-saccharide, protein, lipid and some other bio-molecules, and the compositions and structures of these biological molecules are different between normal cases and pathologic conditions. Based on this principle, someone has already used infrared spectrums to detect cancer cells, for example, first disclosed in Benedetti, Applied Spectroscopy, 1986, 40, 39. However, such detection also requires complex sample preparation techniques, and is time-consuming and invasive. Therefore, there is an urgent need for developing a non-invasive method capable of detecting pathologic changes of organism tissues at early stage.

Fourier transform infrared spectroscopy (abbreviated as FT-IR) is a most widespread method. At present, Fourier transform infrared spectrometers are mainly made up of light source, optical measuring system, computer data processing system, computer interface and electronic circuit system, etc. Among those, the optical measuring system is used for transmitting optical information and detecting and collecting data; the computer is used for processing data and controlling operation of the apparatus. Fourier transform infrared spectrometers can simultaneously transmit lights of all wavelengths to the detector, where the received signal is an interference pattern. After capturing the interference pattern, the computer converts it into a spectrogram by fast Fourier transform method. That is, the different absorption at every wavelength in the interference pattern is discriminated one by one (so-called Fourier transform is that sine or cosine functions in time domain and those in frequency domain are transformed to each other). (see Wu Jinguang, et al., "*Modern Fourier Transform Infrared Spectroscopic Technologies And Applications*", Science and Technology Press, 1994).

FT-IR spectrometers at present exhibit various types and models, such as research type, analytical type, general type and purpose-specific type, and the like. When whichever type of spectrometer is used to detect a sample, a certain amount of the sample to be tested needs to be taken out and then placed onto related attachments inside the sample chamber of the infrared spectrometer to be measured. Sometimes the sample needs to be processed in advance in order to be suitable for measurements, for example, the biological sample is subject to homogenization process and the like. Such method is not only time-consuming, but also incapable of detecting organisms directly. Moreover, it will be an invasive way for the biologic sample measurement. Therefore, it is necessary to improve the Fourier transform infrared spectrometer to have, for example, a dedicated detection apparatus capable of sampling on the surface of organisms and then directly performing measurements, so that it can be directly applied to detect organisms such as human bodies. To do this, since 1995, we have measured and studied various in vitro tumors, in vivo tumors during operations and human body surfaces of tumor regions using the technology of FTIR in connection with mid-infrared fiber optics (Spectroscopy and Spectral Analysis, Vol. 16, No. 5, pp 22-25, October 1996, and ibid, Vol. 24, No. 5, pp 628-630, May 2004). It is found in researches that it is impossible to diagnose states of tumors only by one spectrum detection; also found that fibers of chalcogenide is too fragile and damageable, and fibers of silver halide have short lifetime, all of which are not suitable for clinic usage; and particularly found that infrared spectra of pathologic changes in some gland tumors (in vitro tumor tissues) have same variation regularities as those of corresponding regions non-invasively detected in vivo. Therefore, there exist needs for a method and apparatus and means thereof suitable for clinic usage, which can diagnose the property and the pathologic change degree of a tumor in a region by quickly and non-invasively detecting the infrared spectrum of the corresponding human body surface.

SUMMARY OF THE INVENTION

The first aim of this invention is to establish a non-invasive method for the diagnosis of pathological changes, such as the development of cancer inside a human body, via the FT-IR spectroscopic variation obtained from the surface of a human body.

In order to push this approach into extensive application, the second aim of this invention is to develop a dedicated apparatus suitable for cancer diagnosis via FT-IR spectroscopic measurement during clinical practice.

The dedicated apparatus of the invention is a Fourier Transform infrared spectrometer with a set of additional accessories. The Fourier Transform infrared spectrometer has a measurement range between 4000 $cm^{-1}$ and 400 $cm^{-1}$ and is a compact/portable spectrometer, which has been appropriately modified or newly designed as described below. Non-invasive detection directly performed on the body surface of organisms is designated "in vivo".

The additional accessories of said dedicated apparatus include a mid-IR fiber optics (abbreviated as fiber) sampling attachment, a fiber coupling part, and an infrared detector part as explained below.

1. The fiber sampling attachment is comprised of an incident mid-infrared fiber, an exiting fiber, and an Attenuated Total Reflection (ATR) probe. The incident fiber and exiting fiber are connected by the ATR probe.

The infrared fibers are solid fibers or hollow fibers with a metal coating layer on the internal surface. The diameter of each fiber is 1-3 mm, and their lengths can be arbitrarily set according to clinical requirement. Materials in the solid fibers for transmission of mid-infrared light may be halide, sulfide or mixtures thereof. The spectral range is between 700 $cm^{-1}$ and 4000 $cm^{-1}$.

The ATR probe with a diameter of 3-10 mm may have a tapered shape or be cylindered shape with an inclined section. Materials for the probe may be ZnSe, Ge, ZnS, Si, halide, and sulfide.

To ensure that repeated sterilization of the probe will not affect the performance of the fiber sampling attachment, a sealed design is adopted. That is, a protective layer made of steel, organic or/and inorganic polymer materials (e.g. silicon resin, plastic etc.) are used to shield the optical fiber and the ATR probe.

Based on the principle of attenuated total reflection, the fiber ATR probe contacts the surface of a human body, such as on the body surface of a mammary or parotid gland of a patient, so that FT-IR spectra can be recorded.

2. The fiber coupling part is comprised of an abaxial parabolic mirror and a precise fine-tuning mechanism. It serves to converge the parallel infrared light from the infrared spectrometer into a point with 1-3 mm in diameter so that the light can be coupled into the incident fiber of the fiber sampling attachment effectively.

There are 2 pieces of abaxial parabolic mirrors.

The precise fine-tuning mechanism is a screw position adjustor for adjusting the position of the parabolic mirrors to focus the lights precisely into the optical fiber.

3. The infrared detector part is comprised of an abaxial parabolic mirror, a detector and a 3-dimensional tuning holder.

Among these, the detector can be a liquid nitrogen or electrically cooled MCT detector (tellurium-cadmium-mercury), pyroelectric detector (such as TGS, DTGS, or DLATGS), or photo detector (such as InSb); all of them are available on the market.

The abaxial parabolic mirror converges the parallel light onto the detector. The 3-dimensional tuning holder serves to adjust the infrared light onto the detector thereby maximizing the light energy accepted by the detector so that satisfactory FT-IR spectra with high signal-to-noise ratio (S/N) can be obtained.

The fiber coupling part is placed between an interferometer and the infrared detector. All of them are fixed on an optical table, and the fiber sampling attachment is fixed on the fiber coupling part. The fiber sampling attachment together with the interferometer and the infrared light source constitute an integrated Fourier Transform infrared spectrometer light path system.

These additional accessories of the Fourier Transform infrared spectrometer described above can be manufactured by optical processes and mechanical processes such as milling. Except for those specially mentioned above, materials, structure, and processing involved in procuring the additional accessories are common and familiar to professionals in the field of instrumental manufacture.

Figure 1:
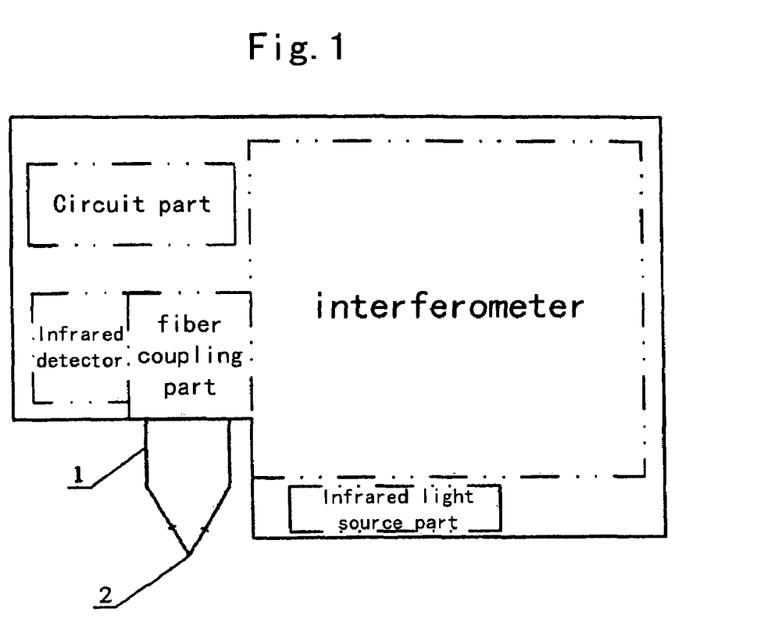
FIGS. 1 and 2 are diagrams illustrating the arrangement and light path of a Fourier Transform infrared spectrometer provided with an additional accessory on the left.
Figure 2:
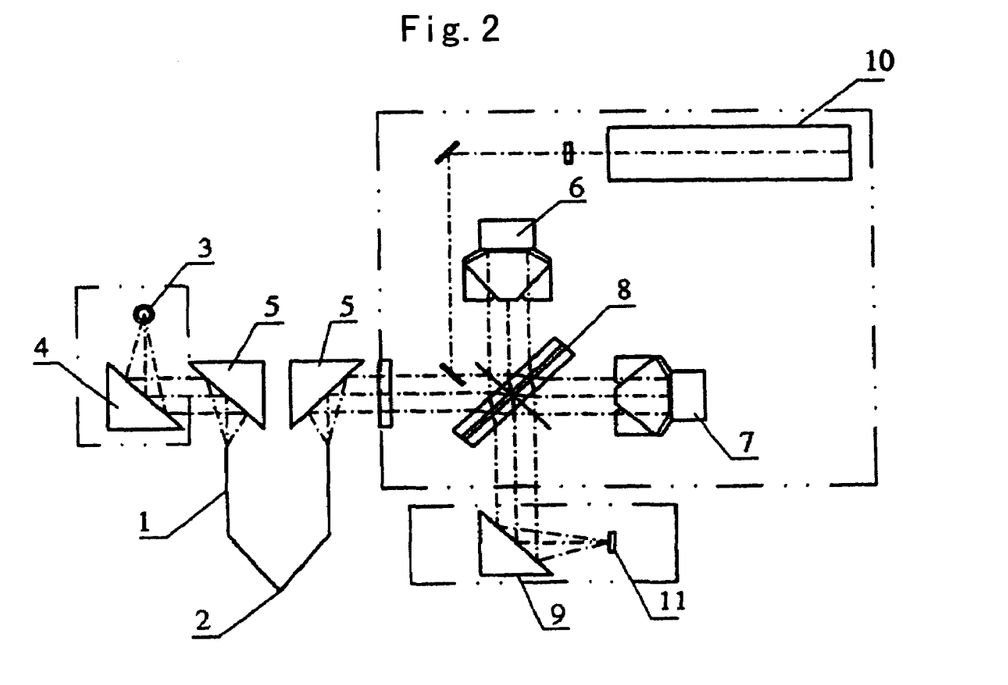
Figure 3:
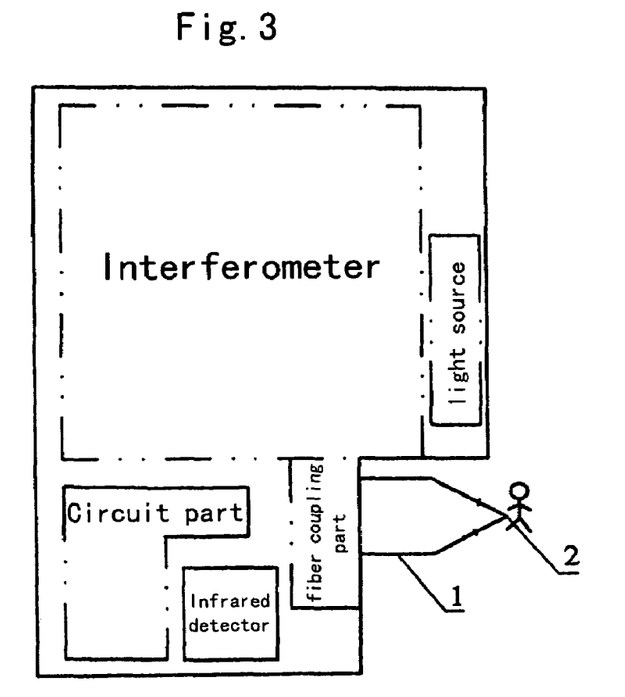
FIGS. 3 and 4 are diagrams illustrating the arrangement and light path of a Fourier Transform infrared spectrometer provided with an additional accessory on the right.
Figure 4:
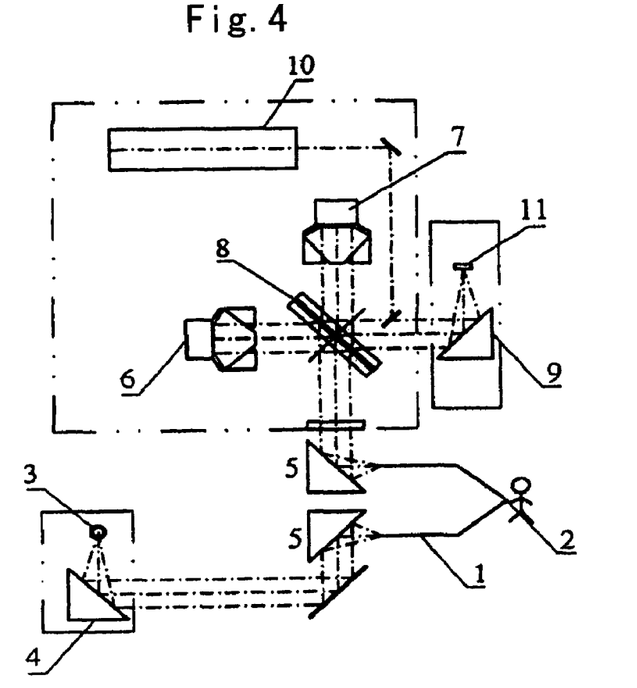
Figure 5:
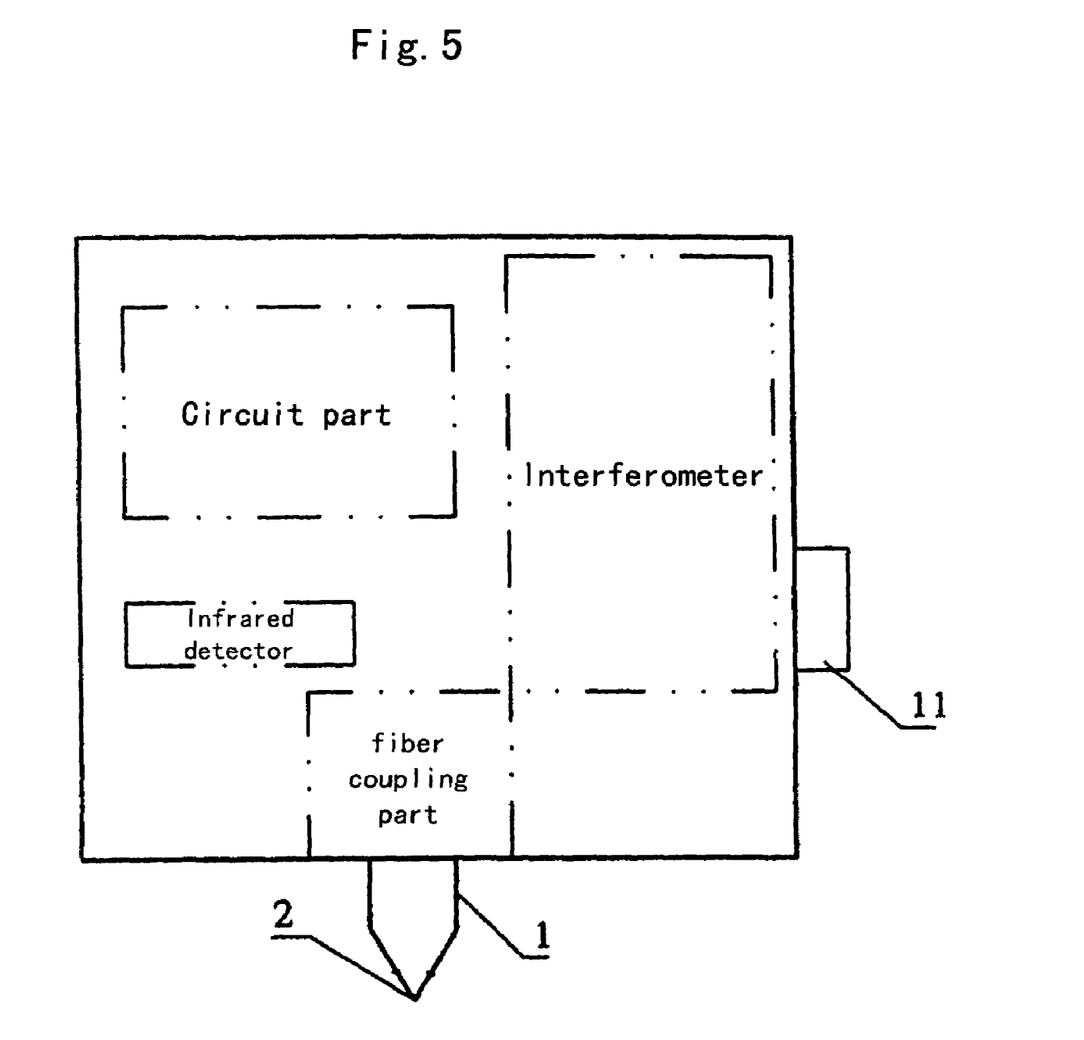
FIG. 5 is a diagram illustrating the arrangement of a Fourier Transform infrared spectrometer provided with an additional accessory in the middle.
Figure 6:
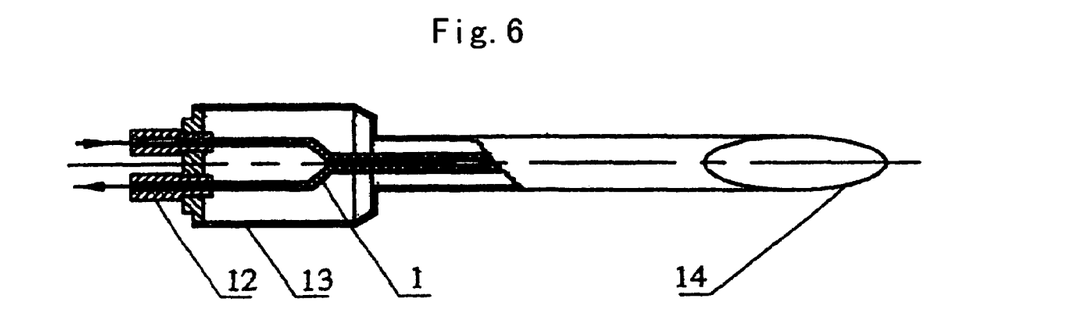
FIGS. 6 and 7 show the ATR probe of cylindered shape with inclined section.
Figure 7:
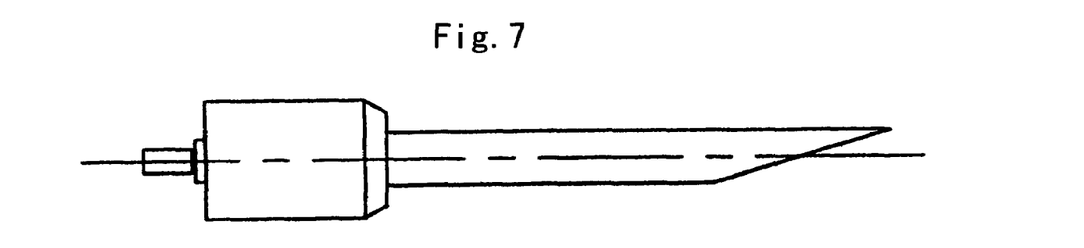
Figure 8:
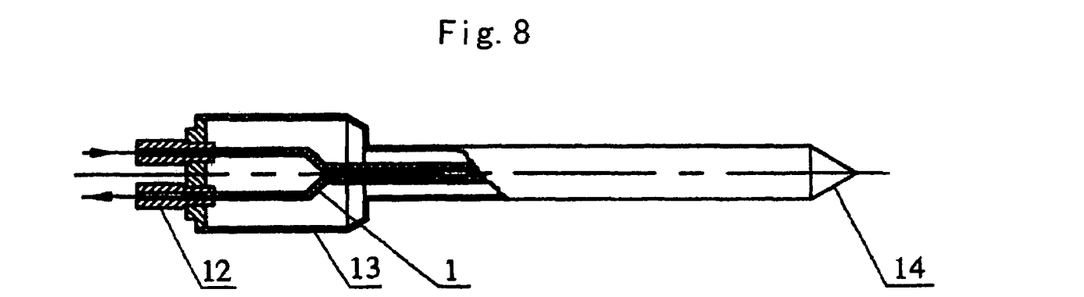
FIGS. 8 and 9 show the ATR probe of tapered shape. Number 12 denotes fiber connectors, 13 denotes the shell of the probe, and 14 denotes the probe made of crystalline materials.
Figure 9:
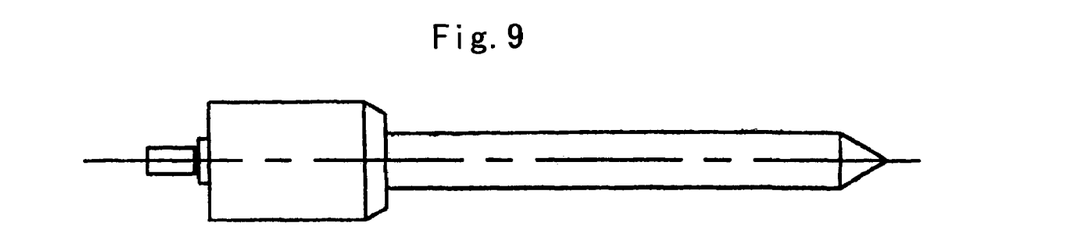

The novel Fourier Transform infrared spectrometer with additional accessories adopts an integrative design in appearance. The additional accessories can be positioned on the left (see FIG. 1, 2), the right (see FIG. 3, 4) or the middle (see FIG. 5) of the Fourier Transform infrared spectrometer, which can be flexibly determined according to actual requirements.

The volume of the novel apparatus and the arrangement of the internal parts can vary. This will not influence the performance and application of the apparatus. However, since the apparatus will be applied in various locations in practical use, it preferably will be as compact and miniaturized as possible. To ensure reliability of the apparatus, the instrument should not have too many internal movable parts.

Considering that the both optical materials in the infrared spectrometer and the obtained spectra are sensitive to moisture, in addition to designing a mechanically sealed interferometer, materials with high humidity resistance such as ZnSe are used to seal the parts in the light path. These parts include the light source, the fiber coupling part and the detector. The sealed apparatus can not only protect the optical parts and the precise rails from dust and humid air as wells as prolong the lifetime of the apparatus, but also can ensure the relative stability under ambient conditions, reduce the influence of the moisture on measured results, and improve the S/N of the obtained spectra. The only remaining standard connector left outside the spectrometer is for connecting to the fiber sampling attachment. In practical use, the fiber sampling attachment can be connected to the connector conveniently.

The measuring procedure is as follows: IR light from light source is conducted out of the spectrometer through the incident optical fiber and passes through the ZnSe ATR probe where the FT-IR spectra of samples are obtained. Then the IR light goes back to spectrometer through the exiting optical fiber.

The infrared light emitted from the infrared light source forms infrared interference light after passing through the interferometer. The infrared interference light enters into the incident fiber of the fiber sampling attachment through the fiber coupling part, which then enters into the (fiber) ATR probe. The fiber ATR probe directly contacts the region to be tested (such as body surface regions of a mammary, parotid, or thyroid gland) for sampling. After sampling, the infrared interference light with infrared spectral information enters into the exiting fiber of the fiber sampling part, goes back to the fiber coupling part, and enters into the detector part through a planar reflector. The detector converts the infrared interference signals into electric signals which then are converted into digital signals by A/D conversion. Finally, the spectrogram (spectrum data) with infrared spectral information about the body tissue tested is obtained by data processing and fast Fourier Transform. If the detection information is processed in connection with dedicated computer software, it is possible to instantly diagnose whether the tested tissue has pathologic changes or not by using output devices such as portable computers.

Detection according to the inventive method is comprised of the following steps:

First, scanning and detecting the ambient air background by the ATR probe; then, placing the probe on the region of the testee's skin surface to be tested. The probe must be in tight contact with the skin to scan. The required resolution of the apparatus is 4 $cm^{-1}$ or 8 $cm^{-1}$, and the number of scans may be more than one. A spectrum that has been compared with the background is obtained, where the range of the spectrum is 800-4000 $cm^{-1}$. It only takes about 2 minutes to complete the entire detection process.

The number of scans depends on actual need. The higher the number of scans, the higher the signal-to-noise ratio (S/N) and the more accurate the results, but this results in a longer time for spectral acquisition. Generally, it is suitable to scan 32 times.

The establishment and judgment of the criteria about whether or not a tissue has pathologic changes is statistically determined on the basis of accumulation of infrared spectral data of tissue with respect to a certain number of healthy persons and patients. For example, by statistical analysis on spectral data of a gland of a number of healthy persons and patients, it is possible to determine the criteria with respect to normal and pathologic spectrum data of the gland and classify the degrees of the pathologic changes. Even though the infrared spectrum of the same pathologic change presents some regular variations among different testees, significant variations among individuals are not present. Moreover, although measurement is carried out on the skin surface, the thickness variation of subcutaneous fat among patients does not substantially affect detection results. Accordingly, these regular variations can be databased into computer software to process the detection information. For example, it is possible to program database processing software for cases and pathologic changes such as hyperplasia of mammary glands to directly give the diagnostic results.

In practical operation, usually this method only requires testing of regions suspected to have pathologic changes, and the resulting spectral data obtained from testing is compared with the established standard spectrum data criteria. It is also possible to differentiate between healthy regions and regions suspected to have pathologic changes for the same subject. For example, when testing the thyroid gland, it is possible to compare the infrared spectra of skin on both sides of the gland. The measured results of the other normal side function as a comparison, and are compared with the established gland spectrum data criteria to determine whether the gland has pathologic changes or not and the degree of the pathologic changes. Generally speaking, the higher the degree of the pathologic change, the more notable the relative variation of characteristic peak intensity.

The inventive method is applicable to detecting molecular changes in structures of living biological tissues, and therefore is capable of diagnosing pathologic changes in tissues at the early stages of cancer. These pathologic changes include tissue hyperplasia, fibroadenoma, malignant tumors and the like. The method is particularly suitable to early diagnosis of pathologic changes in gland regions, such as the mammary gland, the parotid gland and the thyroid gland. In reference to tissue hyperplasia, all of low, intermediate, and high degrees of pathologic changes can be detected. Detection of pathologic changes in gland tissues can infer the presence of cysts and malignant tumors, and additionally testees will not feel uncomfortable during testing.

The operation of the method is simple, quick, accurate, and it doesn't harm the body.

The method is a non-invasive detection method for diagnosing whether or not lumps under body surface skin are cancerous by using infrared spectra, and it only takes 2-3 minutes to obtain spectrum data. Since the peak positions, peak widths, band shapes and relative intensities of spectra for tumor patients are different from those of healthy persons, by studying and analyzing a number of body surface spectrum data, the regularity of variations and the judgment criteria for diagnosis can be obtained. The method is applicable to early diagnosis of some tissue cancerations.

1. The spectral range detected typically is 800-4000 $cm^{-1}$.
2. It is applicable to body surface detection of a plurality of subcutaneous tissue or gland tumors, for example, parotid gland tissues, submaxillary gland tissues, thyroid gland tissues, mammary gland tissues and the like.
3. It is applicable to testing of lumps or detection of pathologic changes on the skin surface.
4. The detection is carried out using a mid-infrared ATR probe.
5. The resolution typically is 4 $cm^{-1}$ (it is also suitable to use 8 $cm^{-1}$ or 2 $cm^{-1}$).

BRIEF DESCRIPTION OF THE DRAWINGS

Numbers 1-5 denote parts of the additional accessories developed as part of the inventive method, wherein, 1 denotes infrared fibers, 2 denotes an ATR probe, 3 denotes an infrared detector, 4 denotes a planar reflector, and 5 denotes abaxial parabolic mirrors.

Numbers 6-10 denote parts originally belonging to the Fourier Transform infrared spectrometer without the additional accessories, wherein, 6 denotes a fixed mirror, 7 denotes a movable mirror, 8 denotes a splitter, 9 denotes a convergence mirror, and 10 denotes a laser.

Number 11 denotes an infrared light source.

DETAILED DESCRIPTION OF PREFERRED EMBODIMENTS

Embodiment 1

Diagnosis of Pathologic Changes in Mammary Glands

Apparatus being used: a dedicated sealed mid-infrared spectrometer, manufactured by Beijing No. 2 Optical Instruments Factory, provided with mid-infrared fibers, an ATR probe and a MCT (tellurium-cadmium-mercury) detector cooled by liquid Nitrogen.

Figure 11:
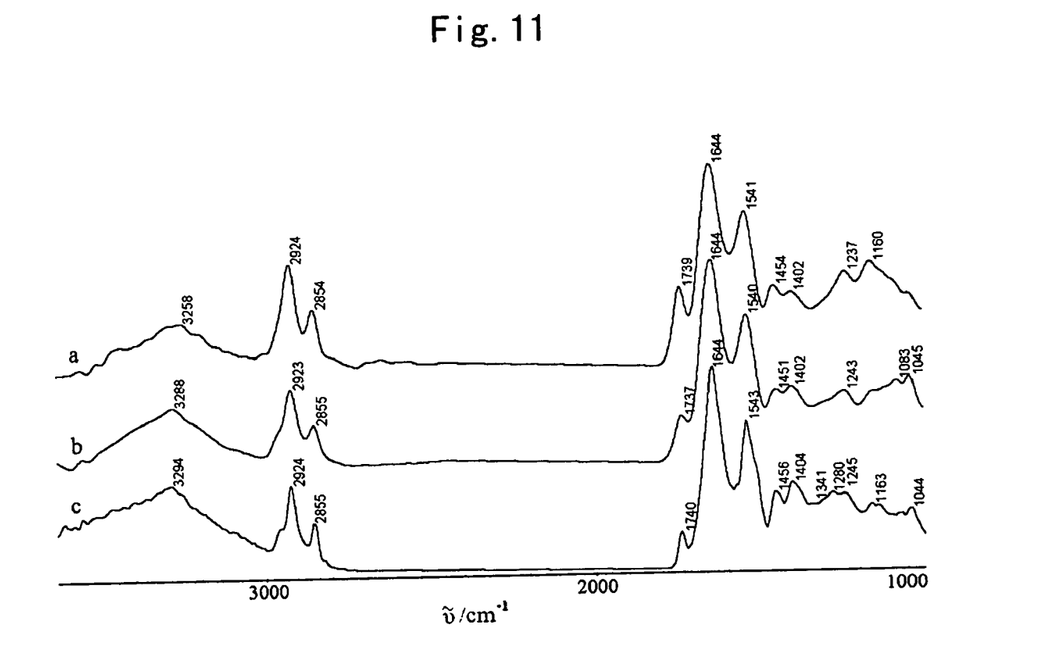
FIG. 11 is a diagram showing example FTIR spectra of (a) a normal mammary gland, (b) a fibroadenoma and (c) a malignant tumor detected in vivo.

Detection Method:

1. Switching on and adjusting to maximize the output energy of the fiber in which the energy coefficient at 2450 $cm^{-1}$ is about 56 (Gain=4).
2. Cleaning the skin of the mammary gland region to be tested with alcohol or water, then placing the ATR probe on the skin of the region to be tested (for patients with mastalgia or touchable lumps, the ATR probe should be placed on the skin outside the pathologic region), scanning and detecting 32 times and based on variations (variations relative to characteristic peaks of normal mammary glands) in characteristic peaks (band of 1000 $cm^{-1}$-1800 $cm^{-1}$ and band of 2800 $cm^{-1}$-3000 $cm^{-1}$) detection of pathologic changes in the mammary gland as seen in comparison with the standard spectrum criteria (as shown in FIG. 11), then diagnosing the degree of the pathologic changes, such as hyperplasia of mammary glands and tumors, and focusing the emphasis of observation on the wave number range of 1400-1490 cm$^{-1}$ to see if there exist distinct differences. For example, variations in peak shape and intensity at ~1460 cm$^{-1}$, ~1400 cm$^{-1}$ can give relevant information for diagnosis.

The characteristic peaks of normal mammary glands are determined based on the testing of a number of healthy mammary glands.

3. In operation, typical clinical methods can be combined with the inventive method, such as detection by hand of a physician. In addition, diagnosis is determined based on the area of the pathologic changes.

Embodiment 2

Diagnosis of Pathologic Changes in Thyroid Glands

In accordance with the method and detection conditions described above as Embodiment 1, the ATR probe is placed on the cleaned surface of the skin outside the thyroid gland on one side. Based on the general regularities of variations in healthy and pathologic spectra concluded from the detection results of a number of patients, and on the differences between spectra in the region of 2800-3800 cm$^{-1}$ and 1000-1800 cm$^{-1}$, it is possible to diagnose the property and the degree of the pathological change of the thyroid gland from a spectrum. For example, variations (relative to characteristic peaks of normal thyroid glands) in peak shape and intensity in 2800-3000 cm$^{-1}$, 1400 cm$^{-1}$-1500 cm$^{-1}$ (mainly observing the band of 1200-1580 cm$^{-1}$) can provide relevant information, which can be inferred by comparison with the standard spectrum data.

Embodiment 3

Diagnosis of Pathologic Changes in Parotid Glands

In accordance with the method and detection conditions described above as Embodiment 1, the ATR probe is placed on the cleaned surface skin outside the parotid glands on both sides (wherein, usually one side is the side with suspected cancerous lumps and the detection results of the other side are used for comparison). As result of comparison, it can be found that there is asymmetry between the spectra on the two sides of a patient with lumps in parotid gland. Based on the general regularities of variations in normal and pathologic spectra concluded from the detection results of a number of patients of different ages and genders, the sensitivity of response in the spectrum is high in the region of 1000-1800 cm$^{-1}$. It is possible to observe whether the parotid tumor is benign or malignant and the degree of deterioration particularly in the range of 1300-1650 cm$^{-1}$. The variations (relative to characteristic peaks of normal parotid gland) in the region of 1200-1580 cm$^{-1}$ are mainly observed, and they are compared with the standard spectral data to diagnose the degree of the pathological changes.

Figure 10:
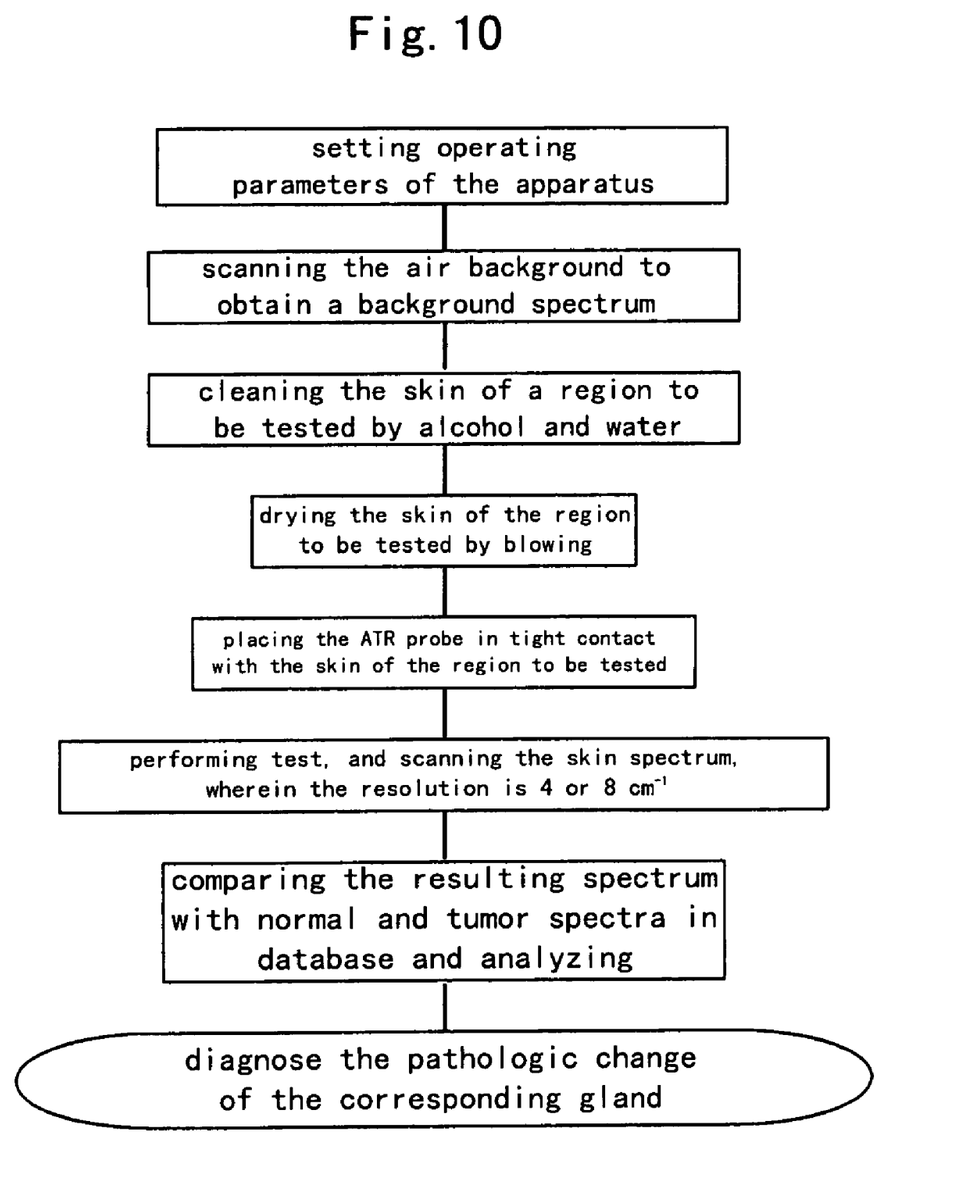
FIG. 10 is a flowchart showing a method for diagnosing tumors according to the inventive method.

Next, the method of the invention is described in connection with the flowchart as shown in FIG. 10.

First, operating parameters of the apparatus are set. Said operating parameters include scanning rate, the number of scans, the resolution of the apparatus, and spectral range.

Then, an air background is scanned to obtain a background spectrum. The skin of the region to be tested is cleaned with alcohol and water, and after the alcohol and the water volatilize, the ATR probe is placed in tight contact with the skin of the region to be tested.

Then, the testing is carried out. The skin spectrum is scanned with a resolution of 2, 4, or 8 cm$^{-1}$. However, it is to be understood that the resolution can be arbitrarily adjusted as desired.

The resulting spectrum is compared with the healthy and tumor spectra in a database and analyzed. FIG. 11 shows examples of FTIR spectra of (a) a normal mammary gland, (b) a fibroadenoma and (c) a malignant tumor detected in vivo.

Finally, diagnose the pathologic change of the corresponding gland.

Although the present invention is described above in detail with reference to the embodiments thereof, it is to be understood that the above embodiments are only for illustrating the invention, and they not intended to restrict the invention. For example, said organism tissue can be the gallbladder, stomach, liver, etc. and the spectrum ranges could be 2800-3800 cm$^{-1}$ and 1000-1800 cm$^{-1}$.

What is claimed is:

1. A dedicated apparatus for detecting changes in molecular structure of human body surface tissue and diagnosing the properties and the degree of pathologic change of a gland tumor in a corresponding region, the apparatus comprising:
   a Fourier Transform mid-infrared spectrometer, used in conjunction with a mid-infrared fiber optics sampling attachment to acquire mid-infrared light reflected from human body surface tissue, wherein the Fourier Transform mid-infrared spectrometer includes:
      an interferometer part for generating mid-infrared light to be provided to the mid-infrared fiber optics sampling attachment;
      an infrared detector part comprising an abaxial parabolic mirror, a detector and a 3-dimensional tuning holder, for maximizing the collection of the mid-infrared light acquired by an ATR probe of the mid-infrared fiber sampling attachment, and for generating mid-infrared spectral data; and
      a data processor for processing the mid-infrared spectral data and comparing the processed infrared spectral data with a tumor database to diagnose the properties and the degree of pathologic change of the tested gland tumor;
   a mid-infrared fiber sampling attachment, connected to a fiber coupling part, wherein the mid-infrared fiber sampling attachment includes a mid-infrared incident fiber, a mid-infrared exiting fiber, and a ZnSe or Ge ATR probe, each of the mid-infrared incident and exiting fibers is a hollow fiber with multiple layers of different coatings on its inside wall, and the ATR probe is of a tapered shape or cylindered shape with an inclined section and is able to acquire an subcutaneous infrared spectrum of the tumor at the body surface when being placed on and in tight contact with the body surface;
   a fiber coupling part, placed between the interferometer part and the infrared detector part of the Fourier Transform infrared spectrometer, wherein the fiber sampling attachment is fixed onto the fiber coupling part, and the fiber coupling part includes two pieces of abaxial parabolic mirrors, as well as reflection mirrors and a precise fine-tuning mechanism for adjusting the parabolic mirrors, the fiber coupling part makes parallel light from the interferometer part converge into a point with a diameter of 1-3 mm so as to couple the converged light into the mid-infrared incident fiber of the fiber sampling attachment, and couples light from the mid-infrared exiting fiber of the fiber sampling attachment into the infrared detector part.

2. The dedicated apparatus as described in claim 1, wherein the Fourier Transform mid-infrared spectrometer uses ZnSe as infrared window material, each part allowing infrared transmission is made of ZnSe.

3. The dedicated apparatus as described in claim 1, wherein the tumor database stores spectral data criterion for diagnosing whether a gland tissue has pathologic changes or not, and is established based on statistical analysis on infrared spectrum data of the tissue of a certain number of healthy persons and patients.

4. The dedicated apparatus as described in claim 1, wherein the mid-infrared incident and exiting fibers used in the fiber sampling attachment have a diameter of 1-3 mm, and a transmitting range of 700-4000 $cm^{-1}$.

5. The dedicated apparatus as described in claim 1, wherein for diagnosis of pathologic changes in the mammary glands, the band widths, peak positions, peak intensities/peak areas, and relative intensity variations of the peaks in the region of 1000 $cm^{-1}$-1800 $cm^{-1}$ and 2800 $cm^{-1}$-3000 $cm^{-1}$ are detected.

6. The dedicated apparatus as described in claim 5, wherein for diagnosis of pathologic changes in the mammary glands, the band widths, peak positions, peak intensities/peak areas, and relative intensity variations of the peaks in the region of 1400 $cm^{-1}$-1490 $cm^{-1}$ are detected.

7. The dedicated apparatus as described in claim 6, wherein for diagnosis of pathologic changes in the mammary glands, variations in band widths, peak positions, and peak intensities/peak areas of 1460 $cm^{-1}$ and 1400 $cm^{-1}$ bands are detected.

8. The dedicated apparatus as described in claim 1, wherein for diagnosis of pathologic changes in the thyroid glands, the band widths, peak positions, peak intensities/peak areas, and relative intensity variations of the peaks in the region of 2800 $cm^{-1}$-3000 $cm^{-1}$ and 1000 $cm^{-1}$-1800 $cm^{-1}$ are detected.

9. The dedicated apparatus as described in claim 8, wherein for diagnosis of pathologic changes in the thyroid glands, the band widths, peak positions, peak intensities/peak areas, and relative intensity variations of the peaks in the region of 2800 $cm^{-1}$-3000 $cm^{-1}$ and 1400 $cm^{-1}$-1500 $cm^{-1}$ are detected.

10. The dedicated apparatus as described in claim 8, wherein for diagnosis of pathologic changes in the thyroid glands, the band widths, peak positions, peak intensities/peak areas, and relative intensity variations of the peaks in the region of 1200 $cm^{-1}$-1580 $cm^{-1}$ are detected.

11. The dedicated apparatus as described in claim 1, wherein for diagnosis of pathologic changes in the parotid and submaxillary glands, the band widths, peak positions, peak intensities/peak areas, and relative intensity variations of the peaks in the region of 1000 $cm^{-1}$-1800 $cm^{-1}$ are detected.

12. The dedicated apparatus as described in claim 11, wherein for diagnosis of pathologic changes in the parotid and submaxillary glands, the band widths, peak positions, peak intensities/peak areas, and relative intensity variations of the peaks in the region of 1200 $cm^{-1}$-1580 $cm^{-1}$ are detected.

13. A method for diagnosing the properties and the degree of pathologic change of a gland tumor in a corresponding region by detecting changes of molecular structure of human body surface tissue comprising of the following steps:
  (1) providing the apparatus as described in claim 1, and selecting operation parameters of the apparatus for detecting the related glands;
  (2) cleaning and sterilizing the ATR probe and the skin of a human body surface to be tested;
  (3) switching on the apparatus, then scanning and recording a spectrum of air acquired by the ATR probe for being used as a background spectrum;
  (4) placing the ATR probe on the skin surface of the region to be tested, the ATR probe being in tight contact with the skin, then using the apparatus to scan and record a spectrum of the cleaned human body surface;
  (5) comparing the recorded spectrum with tumor data in the tumor database to diagnose the properties and the degree of pathologic change of the gland tumor.

14. The method as described in claim 13, wherein for diagnosis of pathologic changes in the mammary glands, the band widths, peak positions, peak intensities/peak areas, and relative intensity variations of the peaks in the region of 1000 $cm^{-1}$-1800 $cm^{-1}$ and 2800 $cm^{-1}$-3000 $cm^{-1}$ are detected.

15. The method as described in claim 14, wherein for diagnosis of pathologic changes in the mammary glands, the band widths, peak positions, peak intensities/peak areas, and relative intensity variations of the peaks in the region of 1400 $cm^{-1}$-1490 $cm^{-1}$ are detected.

16. The method as described in claim 15, wherein for diagnosis of pathologic changes in the mammary glands, variations in band widths, peak positions, peak intensities/peak areas of 1460 $cm^{-1}$ and 1400 $cm^{-1}$ are detected.

17. The method as described in claim 13, wherein for diagnosis of pathologic changes in the thyroid glands, the band widths, peak positions, peak intensities/peak areas, and relative intensity variations of the peaks in the region of 2800 $cm^{-1}$-3000 $cm^{-1}$ and 1000 $cm^{-1}$-1800 $cm^{-1}$ are detected.

18. The method as described in claim 17, wherein for diagnosis of pathologic changes in the thyroid glands, the band widths, peak positions, peak intensities/peak areas, and relative intensity variations of the peaks in the region of 2800 $cm^{-1}$-3000 $cm^{-1}$ and 1400 $cm^{-1}$-1500 $cm^{-1}$ are detected.

19. The method as described in claim 18, wherein for diagnosis of pathologic changes in the thyroid glands, the band widths, peak positions, peak intensities/peak areas, and relative intensity variations of the peaks in the region of 1200 $cm^{-1}$-1580 $cm^{-1}$ are detected.

20. The method as described in claim 13, wherein for diagnosis of pathologic changes in the parotid and submaxillary glands, the band widths, peak positions, peak intensities/peak areas, and relative intensity variations of the peaks in the region of 1000 $cm^{-1}$-1800 $cm^{-1}$ are detected.

21. The method as described in claim 20, wherein for diagnosis of pathologic changes in the parotid and submaxillary glands, the band widths, peak positions, peak intensities/peak areas, and relative intensity variations of the peaks in the region of 1200 $cm^{-1}$-1580 $cm^{-1}$ are detected.

* * * * *